(12) United States Patent
Geisberger et al.

(10) Patent No.: US 7,145,028 B2
(45) Date of Patent: Dec. 5, 2006

(54) CONTINUOUS HYDROSILYLATION PROCESS

(75) Inventors: Gilbert Geisberger, Altoetting (DE); Frank Baumann, Tittmoning (DE); Andreas Daniels, Emmerting (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/288,609

(22) Filed: Nov. 29, 2005

(65) Prior Publication Data

US 2006/0116525 A1    Jun. 1, 2006

(30) Foreign Application Priority Data

Dec. 1, 2004    (DE) ............ 10 2004 058 000

(51) Int. Cl.
  *C07F 7/04*    (2006.01)
(52) U.S. Cl. .................................... 556/479
(58) Field of Classification Search ............... 556/479
  See application file for complete search history.

(56) References Cited

U.S. PATENT DOCUMENTS 6,291,622 B1    9/2001    Dröse et al.
6,350,824 B1    2/2002    Baumann et al.

FOREIGN PATENT DOCUMENTS

| DE | 28 51 456 C2 | 6/1980 |
|---|---|---|
| EP | 0 934 947 A2 | 8/1999 |
| WO | WO 03/014129 | 2/2003 |

OTHER PUBLICATIONS

Derwent Abstract corres. to DE 2 85 1456 [AN 1980-41664C].
Kirk-Othmer, Encyclopedia of Chemical Technology, J. Wiley & Sons, 4th Edition, vol. 20, p. 1007-1059.
English Abstract Corresponding to EP 0 934 947 A2.

*Primary Examiner*—Samuel Barts
(74) *Attorney, Agent, or Firm*—Brooks Kushman P.C.

(57) ABSTRACT

Continuous hydrosilylation of compounds (A) bearing C—C multiple bonds by means of silicon compounds (B) having Si—H groups, in which the reaction components (A) and (B) are reacted continuously in an integrated loop-tube reactor, with reaction mixture being conveyed from the tube into the loop and back again so that a section of the tube is part of the loop circuit, provides a highly controllable reaction process with high product yields.

8 Claims, 1 Drawing Sheet

CONTINUOUS HYDROSILYLATION PROCESS

BACKGROUND OF THE INVENTION

1. Field of the Invention

The invention relates to a process for the continuous hydrosilylation of compounds bearing C—C multiple bonds by means of silicon compounds having Si—H groups.

2. Background Art

The continuous hydrosilylation of H-silanes by means of olefins in loop reactors is described, for example, in DE 2851456 C. The reaction proceeds with good mixing and removal of heat. However, incomplete reaction, secondary reactions of the starting materials and backmixing of the products with the starting materials have to be reckoned with.

U.S. Pat. No. 6,350,824 B describes the continuous hydrosilylation of siloxanes, in which a mixture of the starting materials is passed continuously through a tube reactor. Short residence times can be realized in this way. However, the inadequate energy removal in the case of strongly exothermic reactions leads to secondary reactions, hot spots in the reaction zone and difficult reaction control. It is therefore not possible to achieve either a stable process or stable product quality.

WO 03/014129 describes continuous hydrosilylation using a microreaction technique. Noble metal particles from the catalysts used can block the narrow reaction tubes. The reaction is also difficult to control as a result of pressure buildup and pressure drop in the case of siloxanes which have a relatively high viscosity.

U.S. Pat. No. 6,291,622 B describes a combination of a loop prereactor and a downstream tube reactor. The 2 separate parts of the plant result in the need for a great deal of instrumentation for regulation, associated with higher capital and operating costs. Ratios of starting materials are fixed since only a single-stage reaction takes place. Large amounts of reactive starting materials are present in the reaction system, so that elaborate safety precautions are necessary.

SUMMARY OF THE INVENTION

The invention provides a process for the continuous hydrosilylation of compounds (A) bearing C—C multiple bonds by means of silicon compounds (B) having Si—H groups, in which the reaction components (A) and (B) are reacted continuously in an integrated loop-tube reactor, with the reaction mixture being conveyed from the tube into the loop and back again so that a section of the tube is part of the loop circuit.

DETAILED DESCRIPTION OF THE PREFERRED EMBODIMENT(S)

Figure 1:
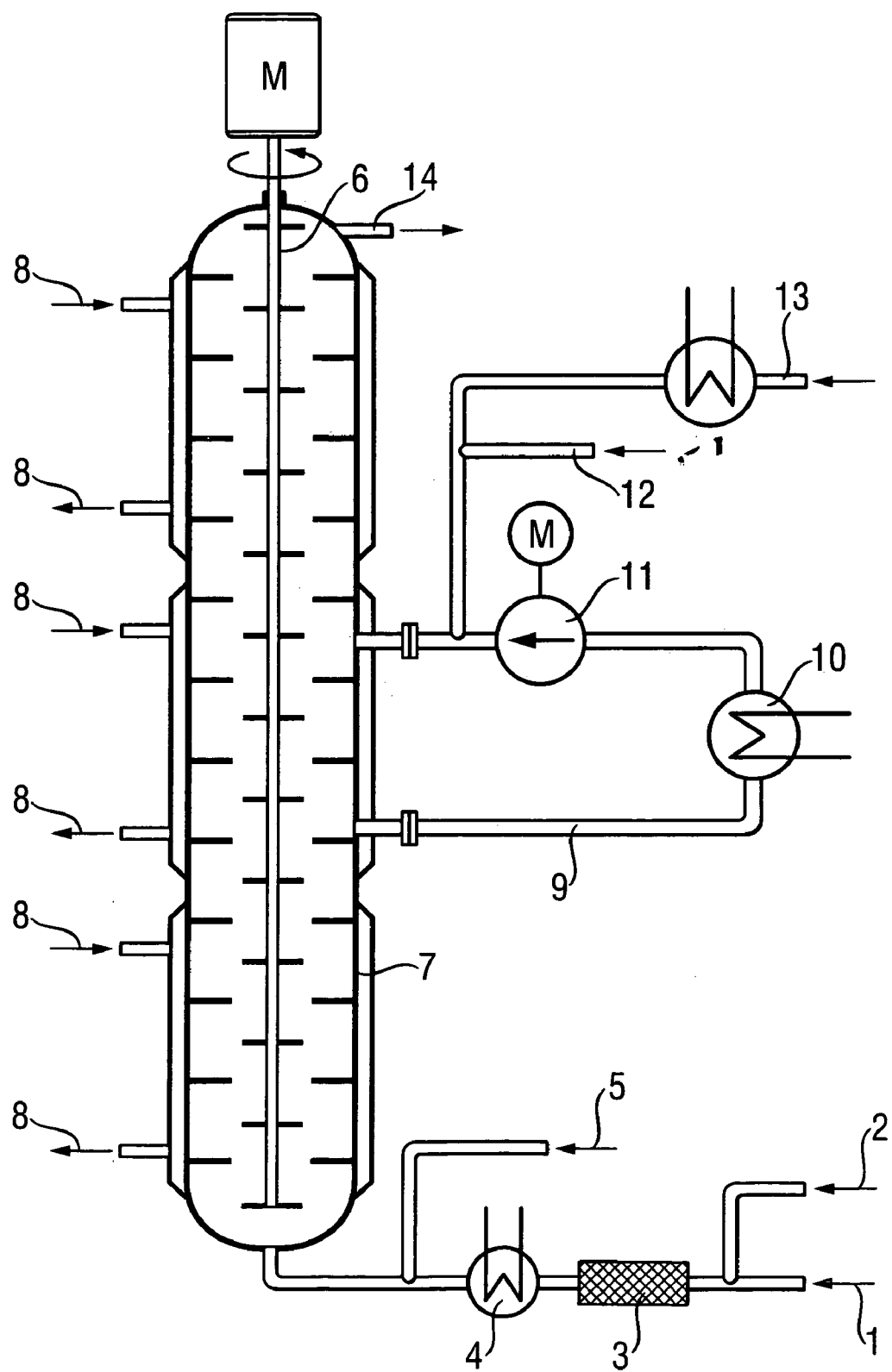
FIG. 1 illustrates one embodiment of an integrated loop-tube reactor.

The inventive process combines the advantages of a loop reactor and a tube reactor. Very good energy removal and mixing of the reaction mixture occurs. Backmixing in the tube reactor is prevented. The starting material reacts completely, so that the product is free of starting material. Constant high product quality can be achieved by means of an easy-to-manage process control system. The time over which starting materials and products are subject to thermal stress can be kept short. Secondary reactions can easily be reduced by this means, and also by variation of the reaction conditions. As a result, off-specification product is avoided and the production costs are reduced; the yields can be increased and the reaction selectivity can be improved.

Relatively small amounts of reactive starting materials are present in the reaction system. The use of solvents can be reduced, and for example in the case of inhomogeneous systems, can be completely dispensed with. The usage of raw materials can be optimized, e.g. by reducing the excess of olefin.

In the loop, the stoichiometry of the compounds (A) and silicon compounds (B) and energy removal can all be readily set. An optimal temperature can be provided set in the subsequent tube reactor for completing the reaction.

Preference is given to conveying at least 10% by mass, more preferably at least 40% by mass, and most preferably at least 80% by mass of the reaction mixture from the tube into the loop.

The compound(s) (A) used in the inventive process can be a silicon-free organic compound having aliphatically unsaturated groups or an organosilicon compound having aliphatically unsaturated groups.

Examples of organic compounds which can be used as component (A) are all types of olefins such as 1-alkenes, 1-alkynes, vinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo[2.2.1]hepta-2,5-diene, 1,3-diisopropenylbenzene, polybutadiene containing vinyl groups, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methylhepta-1,5-diene, 3-phenylhexa-1,5-diene, 3-vinylhexa-1,5-diene and 4,5-dimethyl-4,5-diethylocta-1,7-diene, N,N'-methylenebis(acrylamide), 1,1,1-tris(hydroxymethyl)propane triacrylate, 1,1,1-tris(hydroxymethyl)propane trimethacrylate, tripropylene glycol diacrylate, diallyl ether, diallylamine, diallyl carbonate, N,N'-diallylurea, triallylamine, tris(2-methylallyl)amine, 2,4,6-triallyloxy-1,3,5-triazine, triallyl-s-triazine-2,4,6(1H, 3H ,5H)-trione, diallyl malonate, polyethylene glycol diacrylate, polyethylene glycol dimethacrylate, poly(propylene glycol) methacrylate, allyl glycols, allyl alcohols, allyl polyethers, allyl glycidyl ether and allylsuccinic anhydride.

Furthermore, aliphatically unsaturated organosilicon compounds can be used as constituent (A). If organosilicon compounds which have SiC-bonded radicals bearing aliphatic carbon-carbon multiple bonds are used as constituent (A), they are preferably compounds comprising units of the general formula $$R_a R^1_b SiO_{(4-a-b)/2} \qquad (I),$$

where

R is a radical which is free of aliphatic carbon-carbon multiple bonds, $R^1$ is a monovalent, substituted or unsubstituted, SiC-bonded hydrocarbon radical having an aliphatic carbon-carbon multiple bond, a is 0, 1, 2 or 3 and b is 0, 1 or 2, with the proviso that the sum a+b is ≦4 and that b is 1 or 2 in at least one unit of the general formula (I).

The organosilicon compounds (A) can be silanes, i.e. compounds of the general formula (I) in which a+b=4, or siloxanes, i.e. compounds comprising units of the general formula (I) in which a+b≦3. Mixtures may of course be used as well.

The radical R includes the monovalent radicals —F, —Cl, —Br, —CN, —SCN, —NCO, alkoxy radicals and SiC-bonded, substituted or unsubstituted hydrocarbon radicals which may be interrupted by oxygen atoms or the group —C(O)—.

Examples of radicals R are alkyl radicals such as the methyl, ethyl, n-propyl, isopropyl, n-butyl, isobutyl, tert-butyl, n-pentyl, isopentyl, neopentyl, and tert-pentyl radicals, hexy radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical and octadecyl radicals such as the n-octadecyl radical, cycloalky radicals such as the cyclopentyl, cyclohexyl, cycloheptyl and methylcyclohexyl radicals, aryl radicals such as the phenyl, naphthyl, anthryl and phenanthry radicals, alkaryl radicals such as the o-, m-, p-tolyl radicals, xylyl radicals and ethylphenyl radicals, and aralkyl radicals such as the benzyl radical, and the α- and β-phenylethyl radicals.

Examples of substituted radicals R are haloalkyl radicals such as the 3,3,3-trifluoro-n-propyl radical, the 2,2,2',2',2'-hexafluoroisopropyl radical and the heptafluoroisopropyl radical, and also haloaryl radicals such as the o-, m- and p-chlorophenyl radicals.

The radical R is preferably a monovalent, SiC-bonded, substituted or unsubstituted hydrocarbon radical which is free of aliphatic carbon-carbon multiple bonds and has from 1 to 18 carbon atoms, more preferably a monovalent, SiC-bonded hydrocarbon radical which is free of aliphatic carbon-carbon multiple bonds and has from 1 to 6 carbon atoms, in particular, the methyl or phenyl radical.

The radical $R^1$ can be any group which is able to undergo an addition reaction (hydrosilylation) with an SiH-functional compound. If the radical $R^1$ is an SiC-bonded, substituted hydrocarbon radical, preferred substituents are halogen atoms, cyano radicals, alkoxy groups and siloxy groups. The radical $R^1$ is preferably an alkenyl or alkynyl group having from 2 to 16 carbon atoms, e.g. a vinyl, allyl, methallyl, 1-propenyl, 5-hexenyl, ethynyl, butadienyl, hexadienyl, cyclopentenyl, cyclopentadienyl, cyclohexenyl, vinylcyclohexylethyl, divinylcyclohexylethyl, norbornenyl, vinylphenyl or styryl radical, with particular preference being given to vinyl, allyl and hexenyl radicals.

Preferred component(s) (A) are terminal olefins and allyl-containing, vinyl-containing and alkyne-containing systems, with allyl-containing systems being particularly preferred.

As silicon compound(s) (B), it is possible to use all hydrogen-functional silicon compounds which have also been used hitherto in hydrosilylation reactions. As silicon compound(s) (B) having Si—H groups, preference is given to using compounds comprising units of the general formula

$$R^2{}_c H_d SiO_{(4-c-d)/2} \quad (II)$$

where $R^2$ is as defined above for R, c is 0, 1, 2 or 3 and d is 1 or 2, with the proviso that the sum of c+d is ≦4.

Preference is given to at least two Si-bonded hydrogen atoms being present per molecule.

The silicon compounds (B) used according to the invention can be silanes, i.e. compounds of the general formula (II) in which c+d=4, or siloxanes, i.e. compounds comprising units of the general formula (II) in which c+d≦3, or mixtures thereof. The silicon compounds are preferably organopolysiloxanes, in particular ones comprising units of the general formula (II). The silicon compound (B) used according to the invention preferably comprises Si-bonded hydrogen in an amount in the range from 0.02 to 1.7 percent by weight, based on the total weight of the silicon compound (B).

The molecular weight of the constituent (B) in the case of a siloxane can vary within wide limits, for instance from $10^2$ to $10^6$ g/mol. The constituent (B) can thus be, for example, a relatively low molecular weight SiH-functional oligosiloxane, e.g. tetramethyldisiloxane, or a highly polymeric polydimethylsiloxane having internal or terminal SiH groups or a silicone resin having SiH groups. The structure of the molecules forming the constituent (B) is not fixed either; in particular, the structure of a relatively high molecular weight, i.e. oligomeric or polymeric, SiH-containing siloxane can be linear, cyclic, branched, or resin-like or network-like.

The components (A) and (B) used according to the invention are commercial products or can be prepared by methods customary in chemistry. The ratio of the compounds (A) to silicon compound (B) can be set to any desired value. Preference is given to an excess of compounds (A).

Preference is given to using homogeneous or heterogeneous catalysts. Preferred catalysts are the elements or compounds of Pt, Rh, Pd, Ir. The catalyst can be liquid, solid or be dissolved in suitable solvents or can be present as a fixed-bed catalyst. Particularly suitable amounts of catalyst are from 1 to 500 ppm, more preferably from 2 to 100 ppm, and in particular from 5 to 50 ppm, in each case based on the sum of the masses of compounds (A) and silicon compound (B).

As auxiliaries, it is possible to use, for example, organic solvents in the process.

To illustrate the process, reference will be made below to FIG. 1 in which a preferred variant of the process is depicted.

Silicon compound (B) having Si—H groups (1) and compounds (A) bearing C—C multiple bonds (2) are passed continuously through a premixing chamber (3) and the mixture is preheated in a heat exchanger (4). The heated mixture is admixed with catalyst (5) if appropriate and introduced into the first zone of the reactor provided with a stirring device (6). The tube (7) has 3 zones whose temperatures are regulated separately by means of temperature-control means (8). The outlet to the loop (9) which is provided with heat exchanger (10) and pump (11) is located at the beginning of the middle zone of the tube (7). If required, further reactants, catalysts and auxiliaries can be introduced, if appropriate in preheated form, into the loop (9) via feed lines (12, 13).

The direction of flow in the loop (9) can be chosen freely. The reaction mixture is passed through the last zone of the tube (7) and leaves the reactor via line (14). The point of discharge from the tube (7) into the loop (9) can be chosen freely. The recirculation point is preferably selected so that the remaining section of the tube is sufficient to achieve complete reaction of the starting materials.

In this process, the catalyst can be introduced continuously at different places at different times. Catalyst can, for example, be introduced in the premixing chamber (3) or the first zone or middle zone of the tube (7) or in the loop (9).

The introduction of catalyst can also be effected by means of suitable pump systems. Suitable pump systems are, for example, precision micro metering pumps and piston pumps. The amounts of the catalyst metered in continuously are defined precisely by means of, for example, the free stroke of the micro metering pump. When suitable fluidized-bed catalysts are used, the introduction of catalyst can be omitted.

The starting materials (A), (B) and auxiliaries can be introduced continuously in the required ratio by means of pumps, pressure lines or suction lines. The determination of the amounts can be effected in combination with balances or flow meters. The starting materials can have temperatures of from −20° C. to 100° C., preferably from 0° C. to 60° C. and particularly preferably from 10° C. to 35° C.

When pressure lines and pumps are used, the overall flow process can be controlled by means of the pumps or the line pressure (e.g. nitrogen pressure line), i.e. the residence time of the starting materials in the reaction zones of the continuous reactor is determined by the pumping rate or the applied line pressure.

In the case of a process variant having an upstream, heatable/coolable continuous premixing chamber (3), the feed mixture can be pumped from a separate pump into the continuous loop-tube reactor. In this variant, the residence time of the starting materials in the reaction zones of the continuous reactor can be controlled by means of this one pump.

The mixing of the starting materials in the premixing chamber (3) can be effected by means of suitable mixing devices. Suitable mixing devices include, for example, stirrers and ultrasound. The temperature in the premixing chamber (3) can be chosen freely. It is preferably from 10° C. to 35° C.

In the tube (7), mixing can be effected by means of the stirring device (6), e.g. by means of static mixers or active mixing by stirrers (6) running parallel to the longitudinal axis of the tube (7). These stirrers can be externally driven or be set into motion by the liquid flowing past. Mixing effects and turbulence in the tube (7) can also be achieved by means of fixed or movable baffles at the wall of the tube (7). Mixing in the tube (7) can also be effected by means of installed packing elements. Suitable packing elements are, for example, glass spheres, hollow ceramic or glass bodies, metal turnings, etc.

It is possible to use all customary reactor geometries and shapes as are described, for example, in Kirk-Othmer, ENCYCLOPEDIA OF CHEMICAL TECHNOLOGY, J. Wiley & Sons, 4th edition, Volume 20, pages 1007 to 1059. Particular preference is given to a cylindrical reactor shape whose ratio of diameter to length can be varied as desired, e.g. from 1:10 to 1:2500. The reactor can be positioned as desired. The material of the reactor can vary from metal, e.g. chromium-vanadium steel reactors, enamel steel reactors, through glass reactors.

In the loop (9), mixing can be effected by the stirring device (6), e.g. by means of static mixers or active mixing. These stirrers can be externally driven or be set into motion by the liquid flowing past. Good mixing is also brought about by a high circulation velocity. Further starting materials are preferably added in the loop.

The loop-tube reactor is operated in a temperature range from −50° C. to +400° C., preferably from 0° C. to 250° C. and most preferably from 60° C. to 120° C. Temperature control can be effected by means of suitable heating/cooling temperature-control facilities (8). Suitable temperature-control facilities (8) are temperature-control means (8), e.g. an oil circuit for heating and cooling or two independent cooling and heating circuits based on oil or brine, radiation ovens, heating blowers and vapor heating of any type, e.g. steam heating.

The loop-tube reactor can be run at the abovementioned operating temperatures in an absolute pressure range from vacuum, i.e. 1 mbar, to 300 bar. Preference is given to pressures of from 1 to 150 bar, in particular from 4 to 20 bar.

The throughput, i.e. the amount of starting materials or product passing through per unit time, can vary from 100 g per hour to 10,000 kg per hour of starting materials, depending on reactor size, i.e. reactor length and diameter, reaction parameters, i.e. reaction temperature, viscosity of the starting materials and of the product, heat evolved in the reaction and reaction kinetics. Preference is given to throughputs of from 1 kg per hour to 5000 kg per hour. Particular preference is given to throughputs of starting materials of from 10 kg to 1000 kg per hour.

The throughput can be regulated via three continuous metering units (1), (2) and (13). A further possible way of regulating the throughput of starting material is an electronically controllable or manually operable outlet valve or regulating valve at any point in the loop-tube reactor downstream of the reintroduction of the reaction mixture from the loop (9) or at the end of the tube (7). In this case, the transport devices such as pumps and pressure lines have to work not only against the viscosity of the starting materials and products, but also against a particular constant, freely settable pressure of the installed regulating valve. This type of flow regulation is particularly preferred.

The product quality is preferably monitored continually by "on-line" measurement methods. Suitable measurement methods are all which can detect the conversion of the reaction in a sufficiently short time. These are, for example, spectroscopic measurement methods such as near infrared spectroscopy, FT-IR spectroscopy, Raman and FT-Raman spectroscopy.

The reaction mixture is preferably liquid under the conditions prevailing in the loop-tube reactor. The reaction mixture preferably has a viscosity of not more than 10,000 mPa s.

A single-stage reaction or a multistage reaction can be carried out in the process. A plurality of integrated loop-tube reactors can be connected in series, i.e. a modular configuration of a multistage reaction is possible. Here, the reaction in each reaction stage can be independent of the preceding reaction stage. For example, the continuous hydrosilylation can be followed by further polymer-analogous reactions in a continuous reactor, e.g. amine reactions with epoxides and hydrolysis of esters.

The meanings of all the above symbols of the above formulae are independent of one another. The silicon atom is tetravalent in all formulae. For the purposes of the present invention, unless indicated otherwise, all amounts and percentages are by weight, all temperatures are 20° C. and all pressures are 1.013 bar (abs.). All viscosities are determined at 25° C.

EXAMPLES

Example 1

Loop-Tube Reactor According to the Invention

The reference numerals relate to FIG. 1. A mixture of hydrogenmethylpolysiloxane Me$_3$SiO(HMeSiO)$_{50}$SiMe$_3$ (7.8 kg/h) and alpha-methylstyrene (2.6 kg/h) was passed through a cylindrical stainless steel tube (7) having three heating/cooling zones (V4A steel), an active stirrer (6), a length of 6.7 m and a nominal volume of 7000 ml.

A loop (9) including a heat exchanger (10) was located in the middle zone. 75 ml/h of a 1% strength by weight solution of hexachloroplatinic acid in isopropanol were introduced as catalyst solution into the loop (9) via a feed line (12). As second olefin component, 19.6 kg/h of 1-dodecene were metered in via feed line (12). The pump in the loop conveyed the reaction mixture at 150 l/h and the speed of rotation of the stirrer was 620 rpm. The reaction temperature was 136–142° C. in the entire reactor region. The product contained 2.3–2.6 mol % of unreacted SiH.

Example 2

Tube Reactor Without Loop, Not According to the Invention

A cylindrical stainless steel tube (7) which was analogous to that in Example 1 but did not have a loop and instead had 2 additional introduction points, namely after (downstream of) the first zone and after (downstream of) the middle zone of the tube reactor was used. A mixture of hydrogenmethylpolysiloxane Me$_3$SiO(HMeSiO)$_{50}$SiMe$_3$ (7.8 kg/h) and alpha-methylstyrene (2.6 kg/h) was metered in at the first introduction point at the beginning of the tube reactor (7). 25 ml/h of catalyst solution analogous to that in Example 1 was added at each of the three introduction points. As second olefin component, 1-dodecene was metered in in equal parts (each 9.8 kg/h) after the first and middle zones.

The reaction temperature was in the range from 100 to 190° C. Despite variation of cooling conditions and rates of introduction, the temperature in the middle cooling zone could not be reduced below 160° C., as a result of which part of the 1-dodecene isomerized to 2-dodecene and was no longer available for the desired hydrosilylation reaction. The product contained 4.5–5 mol % of unreacted SiH.

Example 3

Simulated Loop Reactor, Not According to the Invention 1000 g (13.1 mol) of allyl chloride together with 8 g of platinum catalyst (Pt(IV) chloride solution in C$_{12}$-olefin having a platinum concentration of 1% by weight) are placed while stirring in a 5 l autoclave which is operated as a continuous stirred tank (simulation of a loop reactor) and the mixture is heated to 70° C. 2 mol of chlorosilane (Example 3a: methyldichlorosilane=232 g, Example 3b: trichlorosilane=273 g) are subsequently added until the exothermic reaction starts. After a further 11 mol of the chlorosilane (Example 3a: methyldichlorosilane=1276 g, Example 3b: trichlorosilane=1500 g) have been introduced and the parameters pressure and temperature are constant, the following continuous addition rates are set:

1000 g of allyl chloride per hour 8 g of platinum catalyst solution per hour (about 30 ppm)

Example 3a=1500 g of methyldichlorosilane

Target product=chloropropylmethyldichlorosilane

Example 3b=1770 g of trichlorosilane

Target product=chloropropyltrichlorosilane

At the same time, 2500 g of reaction mixture are continuously discharged from the reactor. The samples are taken from the reactor output after 2 hours of continuous operation. The results of the GC analyses are shown in Table 1.

Example 4

Loop-Tube Reactor According to the Invention

The loop-tube reactor described in Example 1 was also used for the silane synthesis. Here, the following amounts were introduced at the following points:

a) Chloropropyltrichlorosilane

Introduction into 1st section of the tube:

| Introduction into 1st section of the tube: | |
|---|---|
| Trichlorosilane: | 12 mol/h (1640 g/h) |
| Allyl chloride: | 15 mol/h (1150 g/h) |
| Platinum catalyst | 6 g/h (approx. 20 ppm) |
| T = 80° C. | |
| Introduction into loop: | |
| Trichlorosilane: | 7 mol/h (960 g/h) |
| Allyl chloride: | 3 mol/h (230 g/h) |
| Platinum catalyst | 5 g/h (approx. 10 ppm) |
| T = 80° C. | |
| Last section of the tube: | |
| T = 100° C. | |

The pressure was in each case the autogenous pressure at the temperature indicated.

b) Chloropropylmethyldichlorosilane

Introduction into 1st section of the tube:

| Introduction into 1st section of the tube: | |
|---|---|
| Methyldichlorosilane: | 12 mol/h (1400 g/h)\ |
| Allyl chloride: | 15 mol/h (1150 g/h) |
| Platinum catalyst | 6 g/h (approx. 22 ppm) |
| T = 80° C. | |
| Introduction into loop: | |
| Methyldichlorosilane: | 7 mol/h (820 g/h) |
| Allyl chloride: | 3 mol/h (230 g/h) |
| Platinum catalyst | 5 g/h (approx. 11 ppm) |
| T = 80° C. | |
| Last section of the tube: | |
| T = 100° C. | |

The pressure was in each case the autogenous pressure at the temperature indicated.

The results of the GC analyses are shown in Table 1:

| | GC analysis data | | | |
|---|---|---|---|---|
| Example | Target product | By-product | Starting silane | Allyl chloride |
| 3a* | 45% | Methyltrichlorosilane 23% Propylmethyldichlorosilane 23% | 8% | — |
| 3b* | 60% | SiCl$_4$ 16% Propyltrichlorosilane 17% | 5% | — |
| 4a | 60% | Methyltrichlorosilane 16% Propylmethyldichlorosilane 17% | 5% | — |
| 4b | 72% | SiCl$_4$ 12% Propyltrichlorosilane 12% | 3% | — |

*not according to the invention

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the continuous hydrosilylation of compounds (A) bearing C—C multiple bonds by means of silicon compounds (B) having Si—H groups, comprising reacting components (A) and (B) continuously in an integrated loop-tube reactor, with reaction mixture being conveyed from the tube into the loop and back again so that a section of the tube is part of the loop circuit.

2. The process of claim 1, wherein constituent (A) comprises silicon-free organic compounds having aliphatically unsaturated groups or organosilicon compounds having aliphatically unsaturated groups.

3. The process of claim 1, wherein compounds comprising units of the general formula $$R^2_c H_d SiO_{(4-c-d)/2} \quad (II),$$

where

R$^2$ is an organic radical which is free of aliphatic carbon-carabon multiple bonds, c is 0, 1, 2 or 3 and d is 1 or 2, with the proviso that the sum of c+d is ≦4 are used as silicon compound (B) having Si—H groups.

4. The process of claim 1, wherein homogeneous or heterogeneous catalysts are used.

5. The process of claim 4, wherein the elements or compounds of Pt, Rh, Pd, Ir are used as catalysts.

6. The process of claim 4, wherein from 1 to 500 ppm of catalysts, based on the sum of the masses of compounds (A) and organosilicon compounds (B), are used.

7. The process of claim 1, wherein the reaction mixture has a viscosity of not more than 10,000 mpa·s.

8. The process of claim 1, wherein further starting materials are added in the loop.

* * * * *